US009072426B2

(12) United States Patent
Zott et al.

(10) Patent No.: US 9,072,426 B2
(45) Date of Patent: Jul. 7, 2015

(54) DEVICE FOR DETECTING AND ILLUMINATING VASCULATURE USING AN FPGA

(71) Applicants: Joseph Zott, Menlo Park, CA (US); Fred Wood, Medford, NY (US); Dmitriy Yavid, Stony Brook, NY (US); Seung P Kim, Seoul (KR); Klaus Zietlow, Piedmont, CA (US)

(72) Inventors: Joseph Zott, Menlo Park, CA (US); Fred Wood, Medford, NY (US); Dmitriy Yavid, Stony Brook, NY (US); Seung P Kim, Seoul (KR); Klaus Zietlow, Piedmont, CA (US)

(73) Assignee: AccuVein, Inc, Cold Spring Harbor, NY (US)

( * ) Notice: Subject to any disclaimer, the term of this patent is extended or adjusted under 35 U.S.C. 154(b) by 0 days.

(21) Appl. No.: 13/957,767

(22) Filed: Aug. 2, 2013

(65) Prior Publication Data
US 2014/0039321 A1    Feb. 6, 2014

Related U.S. Application Data

(60) Provisional application No. 61/678,726, filed on Aug. 2, 2012.

(51) Int. Cl.
A61B 6/00 (2006.01)
A61B 5/00 (2006.01)
A61B 5/02 (2006.01)
A61B 5/107 (2006.01)

(52) U.S. Cl.
CPC .............. *A61B 5/0033* (2013.01); *A61B 5/743* (2013.01); *A61B 5/02007* (2013.01); *A61B 5/1075* (2013.01); *A61B 5/1077* (2013.01); *A61B 5/1079* (2013.01); *A61B 5/004* (2013.01); *A61B 5/745* (2013.01)

(58) Field of Classification Search
USPC .......................................... 600/407, 473, 476
See application file for complete search history.

(56) References Cited

U.S. PATENT DOCUMENTS

| | | |
|---|---|---|
| 3,527,932 A | 9/1970 | Thomas |
| 4,185,808 A | 1/1980 | Donohoe et al. |
| 4,265,227 A | 5/1981 | Ruge |
| 4,312,357 A | 1/1982 | Andersson et al. |
| 4,495,949 A | 1/1985 | Stoller |
| 4,699,149 A | 10/1987 | Rice |
| 4,766,299 A | 8/1988 | Tierney et al. |
| 4,771,308 A | 9/1988 | Tejima et al. |
| 4,780,919 A | 11/1988 | Harrison |
| 5,146,923 A | 9/1992 | Dhawan |
| 5,418,546 A | 5/1995 | Nakagakiuchi et al. |
| D362,910 S | 10/1995 | Creaghan |
| 5,504,316 A | 4/1996 | Bridgelall et al. |
| 5,598,842 A | 2/1997 | Ishihara et al. |
| 5,610,387 A | 3/1997 | Bard et al. |
| 5,719,399 A | 2/1998 | Alfano et al. |
| 5,756,981 A | 5/1998 | Roustaei et al. |
| 5,787,185 A | 7/1998 | Clayden |
| 5,847,394 A | 12/1998 | Alfano et al. |
| 5,929,443 A | 7/1999 | Alfano et al. |

(Continued)

FOREIGN PATENT DOCUMENTS

GB    1298707    5/1970
KR    2003/0020152 A    3/2003

*Primary Examiner* — James Kish
(74) *Attorney, Agent, or Firm* — Thomas A. O'Rourke; Bodner & O'Rourke, LLP

(57) ABSTRACT

A laser based vascular illumination system utilizing a FPGA for detecting vascular positions, processing an image of such vasculature positions, and projecting the image thereof onto the body of a patient.

12 Claims, 8 Drawing Sheets

(56) References Cited

U.S. PATENT DOCUMENTS

| | | |
|---|---|---|
| 5,947,906 A | 9/1999 | Dawson, Jr. et al. |
| 5,969,754 A | 10/1999 | Zeman |
| 6,141,985 A | 11/2000 | Cluzeau et al. |
| 6,142,650 A | 11/2000 | Brown et al. |
| 6,301,375 B1 | 10/2001 | Choi |
| 6,314,311 B1 | 11/2001 | Williams et al. |
| 6,438,396 B1 | 8/2002 | Cook et al. |
| 6,463,309 B1 | 10/2002 | Ilia |
| 6,650,916 B2 | 11/2003 | Cook et al. |
| 6,719,257 B1 | 4/2004 | Greene et al. |
| 7,302,174 B2 | 11/2007 | Tan et al. |
| D566,283 S | 4/2008 | Brafford et al. |
| 7,431,695 B1 | 10/2008 | Creaghan |
| 7,532,746 B2 | 5/2009 | Marcotte et al. |
| 7,904,138 B2 | 3/2011 | Goldman et al. |
| 7,925,332 B2 | 4/2011 | Crane et al. |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Timocszyk et al. |
| 8,364,246 B2 | 1/2013 | Thierman |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,548,572 B2 | 10/2013 | Crane et al. |
| 8,649,848 B2 | 2/2014 | Crane et al. |
| 2003/0125629 A1 | 7/2003 | Ustuner |
| 2004/0015158 A1 | 1/2004 | Chen et al. |
| 2004/0046031 A1 | 3/2004 | Knowles et al. |
| 2004/0222301 A1 | 11/2004 | Willins et al. |
| 2005/0131291 A1 | 6/2005 | Floyd et al. |
| 2005/0146765 A1 | 7/2005 | Turner |
| 2005/0168980 A1 | 8/2005 | Dryden et al. |
| 2006/0020212 A1 | 1/2006 | Xu |
| 2006/0173351 A1 | 8/2006 | Marcotte et al. |
| 2006/0184040 A1 | 8/2006 | Keller et al. |
| 2007/0161907 A1* | 7/2007 | Goldman et al. ............ 600/476 |
| 2008/0194930 A1 | 8/2008 | Harris et al. |
| 2010/0061598 A1* | 3/2010 | Seo ............................. 382/115 |
| 2011/0112407 A1* | 5/2011 | Wood et al. .................. 600/476 |
| 2011/0125028 A1* | 5/2011 | Wood et al. .................. 600/476 |
| 2014/0039309 A1 | 2/2014 | Harris et al. |
| 2014/0046291 A1 | 2/2014 | Harris et al. |

* cited by examiner

Vein Algo Architecture

2-D Moving Window Sum Generator

Latency = X-Sum Buffer Size + Y-Sum Buffer Size

X-Sum Buffer Size = (boxsize - 1)*(number_of_horizontal_pixels) ;
Y-Sum Buffer Size = (boxsize - 1);

X-sum generator (Boxsize – 1) stage shift register

DEVICE FOR DETECTING AND ILLUMINATING VASCULATURE USING AN FPGA

CROSS REFERENCES TO RELATED APPLICATIONS

This application claims priority on U.S. Provisional Application Ser. No. 61/678,726 filed on Aug. 2, 2012, the disclosures of which are incorporated herein by reference.

BACKGROUND

Summary

A laser based vascular illumination system utilizing a FPGA for detecting vascular positions, processing an image of such vasculature positions, and projecting the image thereof onto the body of a patient.

BRIEF DESCRIPTION

FIG. 1 Block diagram of a system for detecting and illuminating the vasculature in a patient.
FIG. 2 Shows the signal processing flow of the FPGA.
FIG. 3 shows the internal bus architecture of the FPGA.
FIG. 4 shows details of the vein processing.
FIG. 5 shows the vein processing at the boundary of the image frames.
FIG. 6 shows further detail of the vein processing at the boundary of the image frames.
FIG. 7 2-D Moving Window Sum Generator.
FIG. 8 shows a X-sum generator.

DETAILED DESCRIPTION

FIG. 1 shows a block diagram of a system for detecting and illuminating the vasculature in a patient The system shown in the block diagram of FIG. 1 is used for detecting the location of veins on a patient and illuminating the veins.

The disclosures of U.S. patent application Ser. No. 12/804,506, now issued as U.S. Pat. No. 8,463,364 are incorporated herein by reference.

In a preferred embodiment, FIGS. 30-47 of application Ser. No. 12/804,506 illustrates an assembly of a housing that may be used in the present invention. In the present invention, circuit boards 43, 44 and 15 of application Ser. No. 12/804,506 may be modified to contain the circuitry described by the block diagram in FIG. 1. The remainder of the device in FIGS. 30-47 can remain substantially the same.

In FIG. 1 an FPGA 1 (field programmable gate array) is configured to control a red laser drive 2 which in turn drives a red laser 3. The output of the red laser 3 is controlled in a manner so as to illuminate the detected veins. A red laser feedback 4 detects the output of the red laser 3 and sends the information to the FPGA 1. Accordingly, a closed loop is formed whereby the FPGA 1 can both drive the Red laser 3 and receive feedback as to the red laser 3 state.

FPGA 1 outputs data to an IR laser drive 5 which in turn drives an IR laser 6. The output of the IR laser 6 is controlled to output an intensity of IR light, aimed at the area of the body where veins are located, sufficient to detect the veins. An IR laser feedback 7 detects the output of the IR laser 6 and sends the information to the FPGA 1. Accordingly, a closed loop is formed whereby the FPGA 1 can both drive the IR Laser 6 and receive feedback as to the IR laser 6 state.

FPGA 1 communicates to both a x-mirror drive 8 and a y-mirror drive 9 to drive x-mirror 10 and y-mirror 11 in such a manner that a raster pattern is formed on the patient when the Red laser 3 and the IR laser 6 are coaxially projected thereon. X-mirror feedback 12 and y-mirror feedback 13 detect the positions of the x-mirror 10 and y-mirror 11, respectively, and communicates such information to the FPGA 1.

Top photodiode 23 and bottom photodiode 22 receive the IR Laser 6 reflected off the patient, converts the light into an analog signal which is provided to Top FE 25 and Bottom FE 24, and then to Top ADC 27 and bottom ADC 25, respectively. The top FE 25 and the bottom FE 24 are front end circuits that provide analog filtering, gain control and threshold of the analog signals. The Top ADC 27 and bottom ADC 26 are analog to digital converters that convert the analog signals to digital representations thereof to be communicated to the FPGA 1. Control lines are provided from the FPGA 1 to the top FE 25 and the bottom FE 24 to set parameters such as, for example, gain control and analog filtering.

From a mechanical standpoint, the red laser 3 and the IR laser 6 are co axially aligned and projected off of mirrors X-mirror 10 and Y-mirror 11 to form a pattern, such as for example, a raster pattern on the patient. The IR laser 6 reflects off the patient and is received by top photodiode 23 and photodiode 22. The reflected IR light contains information as to the location of the veins (IR light is absorbed by the blood in the veins and therefore the amount or reflected IR light is lower when the IR laser 6 is aimed at a vein. The FPGA 1 time sequentially receives in the signal form the top ADC 27 and the bottom ADC and can form two partial and/or full frame images of the reflected IR light (hereinafter a top channel data and a bottom channel data wherein the top channel data is received from the top ADC 27 and the bottom channel data is received from the bottom ADC). The FPGA 1 processes one or both of the partial and/or full image to detect and enhance the image of the veins. The enhanced image is time sequentially projected by the Red laser 3 onto the patient.

A CPLD is provided for controlling an LCD 19 with displays user information related to the operating status of the device. It also controls an audio 20 output to provide audible tones to the user. Finally the CPLD 18 controls the switches 21 on the unit for turning on and off the units as well as selecting user modes and entering data.

A microprocessor PIC MCU 17 is provided for receiving and monitoring the IR laser feedback 7 signal, the red laser feedback 4 signal, the x-mirror feedback 12 signal and the y-mirror feedback 13 signal. Since these signals are also provided to the FPGA 1, redundancy monitoring of the signals is provided by the PIC MCU 17. This is particularly important when regulatory requirements require redundant monitoring of the laser power and movement to comply with safety requirements. The PIC MCU 17 also monitors the device power management 14, the Li-ion Battery management 15 circuitry and the Li-ion Fuel gauge 16.

FIG. 2 Shows an example of the signal processing flow of the FPGA

FIG. 2 shows an embodiment of the signal processing algorithm of the FPGA of FIG. 1. As described with reference to FIG. 1, the image of the reflected IR laser 6 is time sequentially stored in the FPGA 1 as top channel data 30T and bottom channel data 30B.

The X-mirror 10 oscillates about a single axis to move the laser beam from the IR laser 6 to form a line. The beam moves first in one direction and then back in the other direction. It is critical that the left to right image data be in convergence with the right to left data. The top line correlator 31T measures the shift in the convergence of the top channel data 30T and supplies the information to the mirror convergence control 34. Similarly, the bottom line correlator 31B measures the shift in the convergence of the bottom channel data 30B and supplies the information to the mirror convergence control 34. The mirror convergence control 34 can adjust the control signals provided from the FPGA 1 to the x-mirror drive 8 so as to converge the data.

A top histogram 32T receives the top channel data 30T and generates a histogram based upon an entire frame of the top channel data 30T. Similarly, a bottom histogram 32B receives the top channel data 30B and generates a histogram based upon an entire frame of the bottom channel data 30B. The histograms contain information describing the characteristics of the images, including but not limited to contrast and intensity levels. The top histogram 32T and the bottom histogram 32B are provided to exposure control 35. Exposure control 35 communicates appropriate signals the IR laser drive 5 to adjust the power of the IR laser 6 on a frame by frame basis until the histograms indicate appropriate images. The exposure control 35 also communicates with the top FE 25 and bottom FE 24 to adjust parameters such as setting thresholds and setting electrical gain.

A top vein processing 33T block receives the top channel data 30T and performs image processing to detect vein patterns and provides the enhanced vein image to fused vein projection 36. Similarly, bottom vein processing 33B block receives the bottom channel data 30B and performs image processing to detect vein patterns and provides the enhanced vein image to fused vein projection 36. The fused vein projection 36 forms a single image and communicates the Image to the alpha blended projection 38. The fused vein projection 36 can form the single image by merging the images from the top vein processing 33T and bottom vein processing 33B. Alternative, the fused vein projection 36 can simply select the best image received from the top vein processing 33T and the bottom vein processing 33B.

Alpha channel 37 forms an image that contains graphical data, such as text or characters. Alpha channel 37 and fused vein projection 36 are provided to alpha blended projection 38 with drives the IR laser drive 5 to display an image which is the combination of the fused vein projection 36 and the alpha channel 37.

Figure 1:
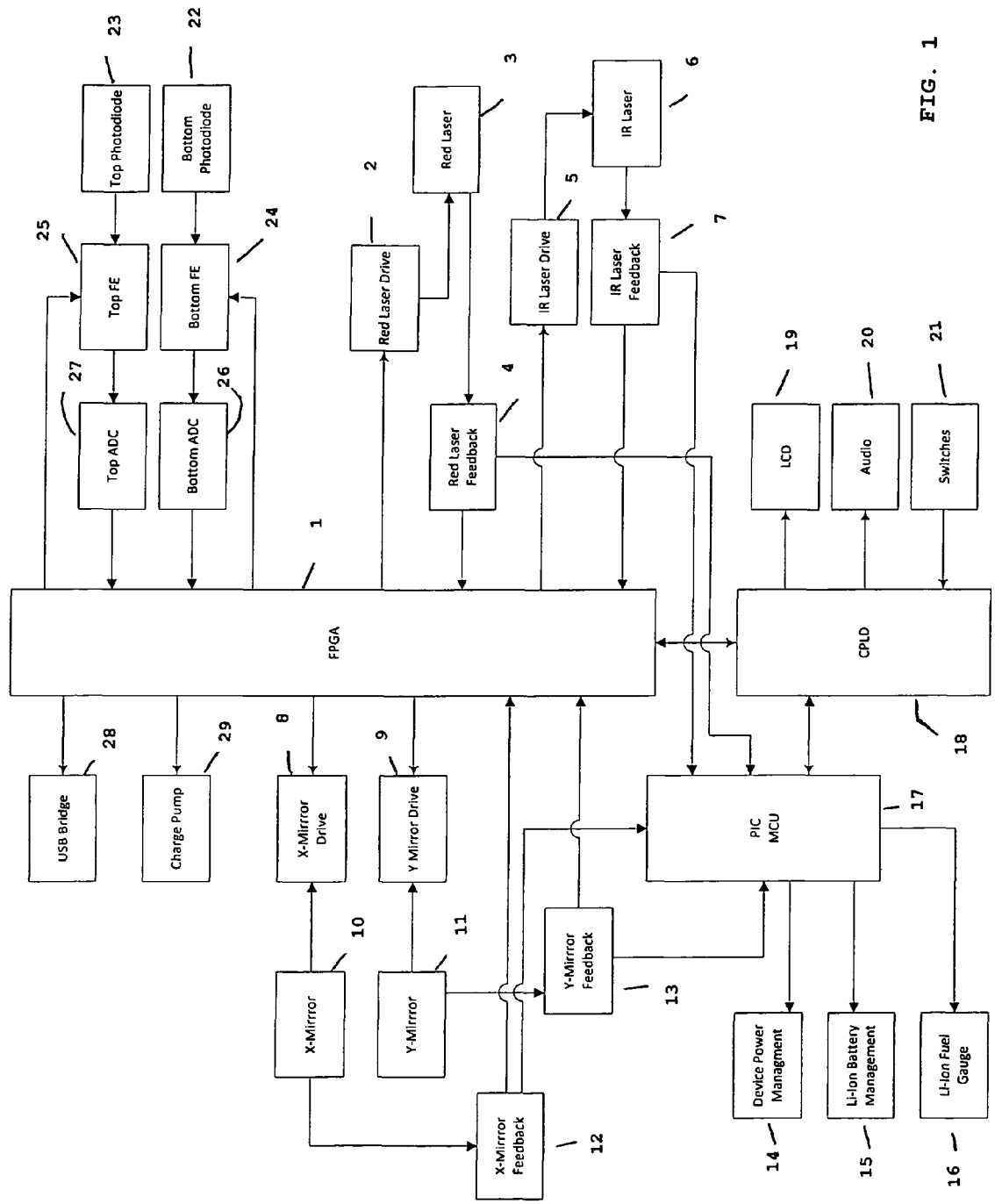
Figure 2:
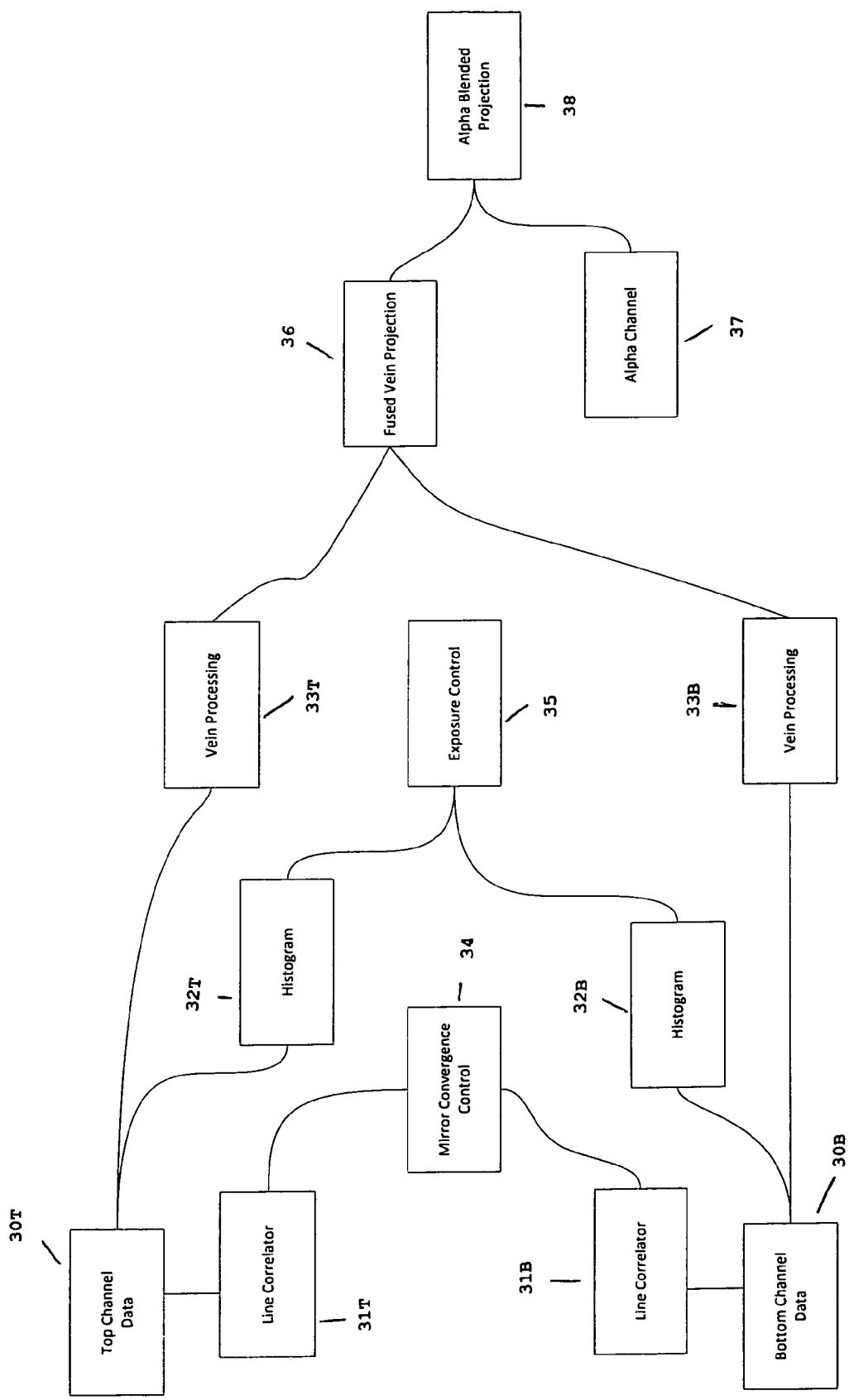
Figure 3:
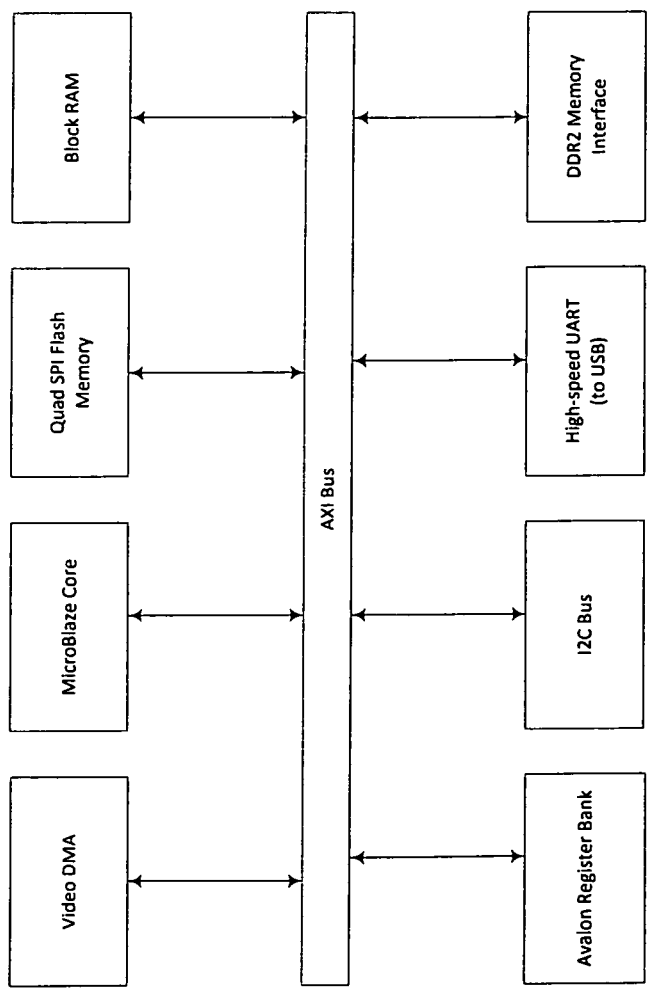
FIG. 3 shows an example of the internal bus architecture of the FPGA
Figure 4:
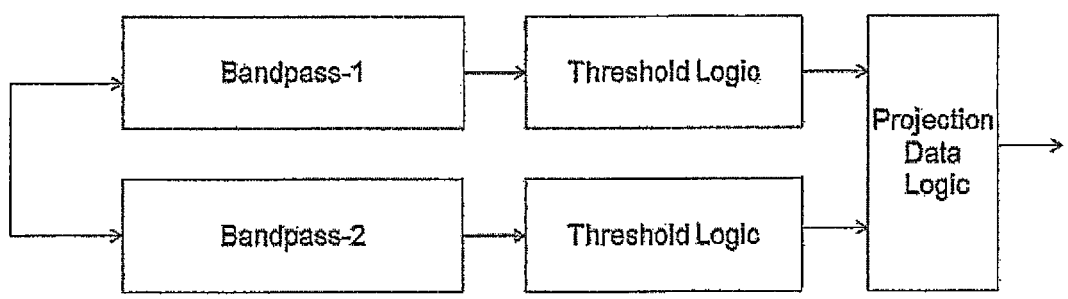
FIG. 4 shows details of the top vein processing 33T and bottom vein processing 33B.
Figure 5:
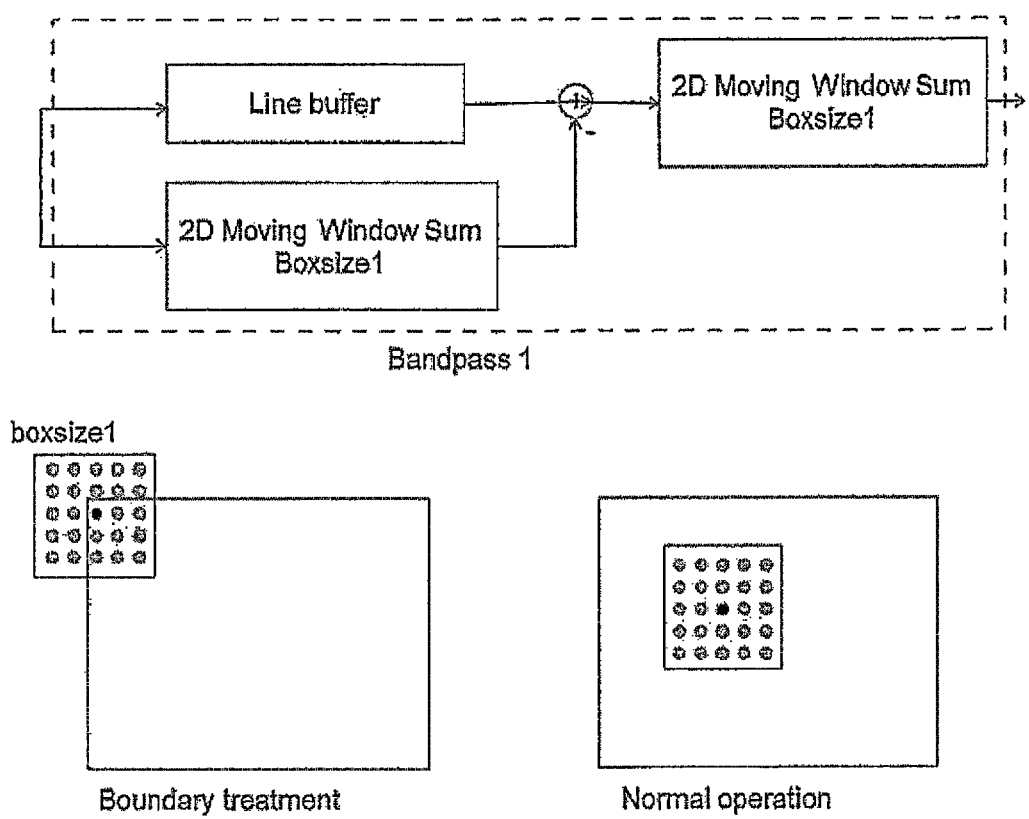
FIG. 5 shows the vein processing at the boundary of the image frames.
Figure 6:
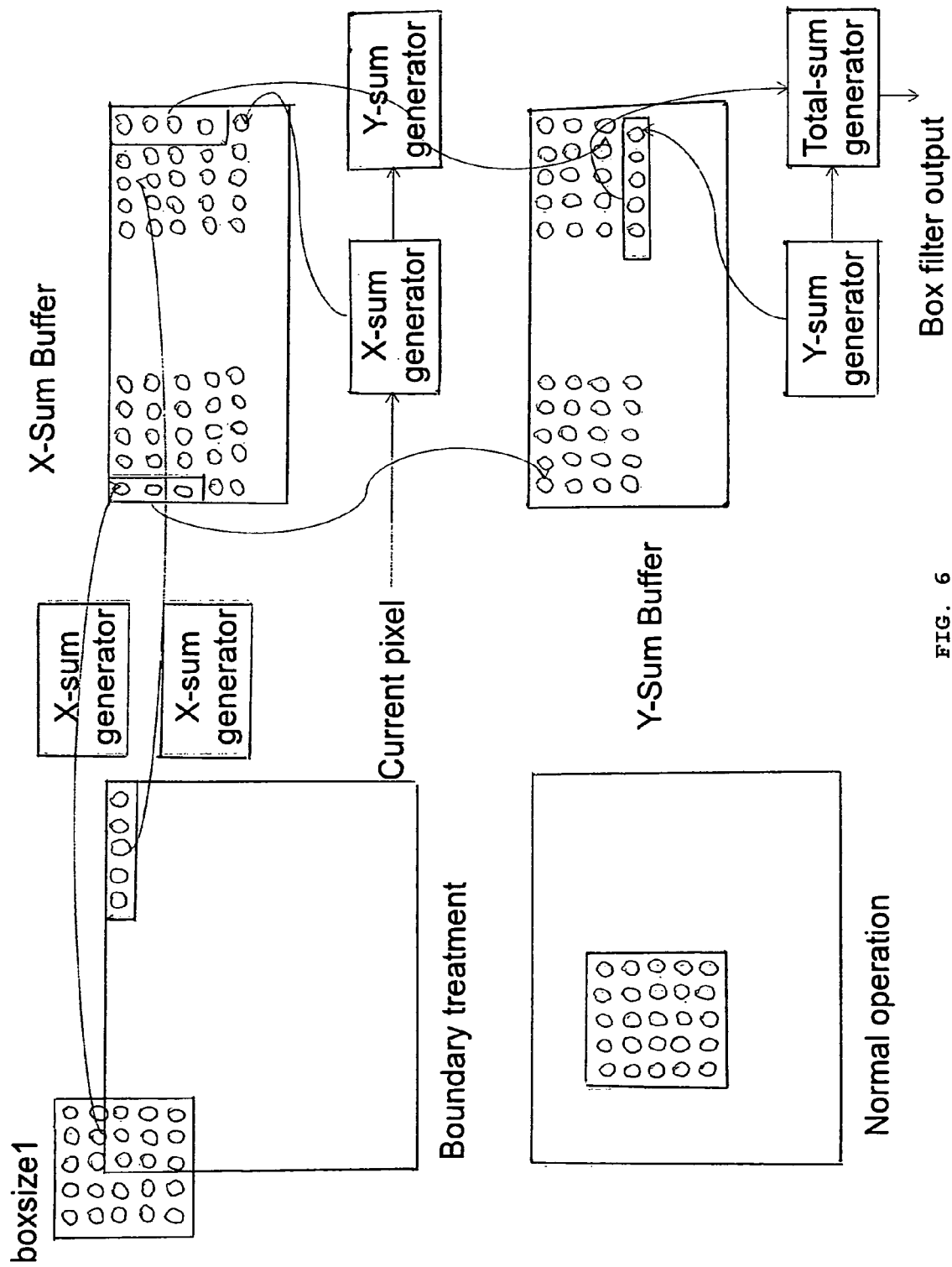
FIG. 6 shows further detail of the vein processing at the boundary of the image frames.
Figure 7:
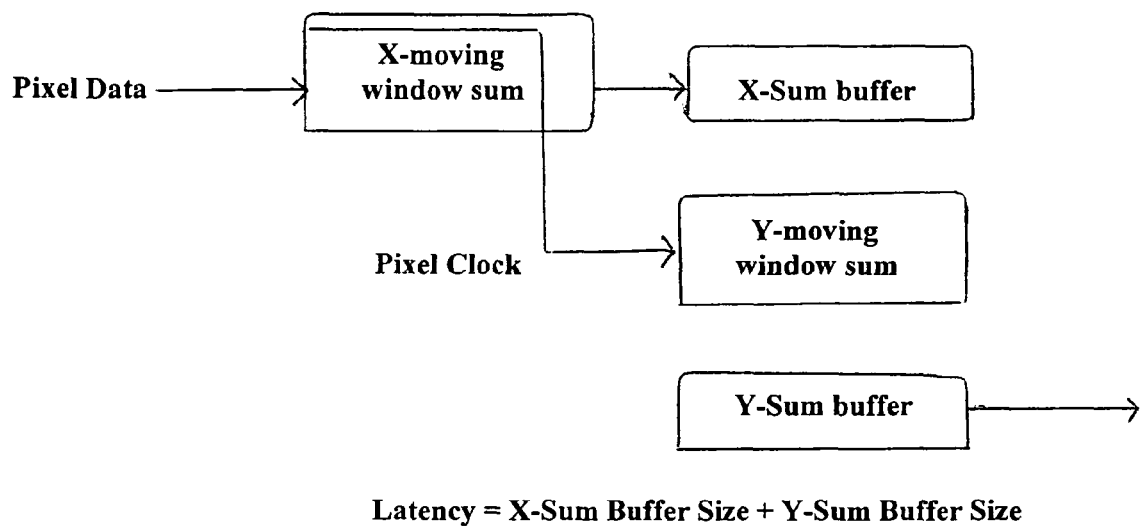
FIG. 7 shows the 2-D Moving Window Sum Generator.
Figure 8:
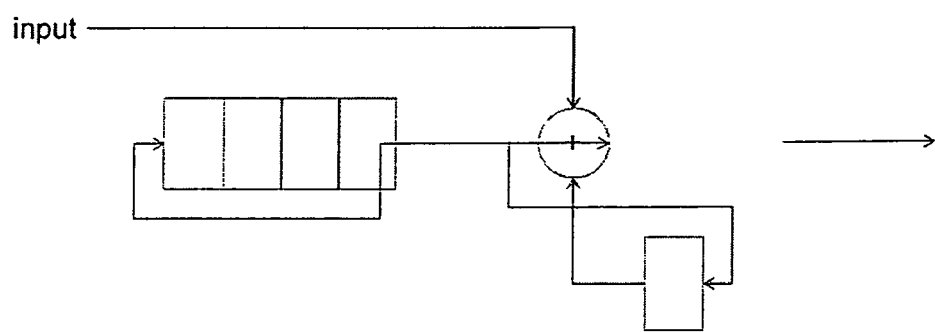
FIG. 8 shows a X-sum generator.

We claim:

1. An improved laser-based illumination system comprising:
   a field programmable gate array (FPGA);
   an X-direction mirror configured to oscillate about a first axis in a first direction and in a second direction, and an X-direction mirror drive;
   a Y-direction mirror configured to oscillate about a second axis in a third direction and in a fourth direction, and a Y-direction mirror drive;
   an X-direction mirror feedback and a Y-direction mirror feedback, each configured to detect a current respective mirror position and to signal said current position to said FPGA;
   an infrared laser and an infrared laser drive, said FPGA configured to control said infrared laser to control said infrared laser;
   an infrared laser feedback configured to detect the output of said infrared laser, and to signal said detected output to said FPGA;
   a red laser and a red laser drive, said red laser configured to project a beam of light coaxially with a beam of light from said infrared laser, said FPGA configured to control said red laser drive to control said red laser;
   a red laser feedback configured to detect the output of said red laser, and to signal said detected output to said FPGA;
   wherein said FPGA is further configured to control said X-direction mirror drive for said X-direction mirror to reflect said coaxial beam of light in a line, in both said first direction and said second direction, and said FPGA further configured to control said Y-direction mirror drive for said Y-direction mirror to oscillate about said second axis, to reflect said line of light to generate a raster pattern;
   a top line correlator and a bottom line correlator, each said top and bottom line correlators configured to measure a respective shift in convergence between said reflected line of light in said first direction and said second direction, for each said oscillation of said X-direction mirror;
   a mirror convergence control, said mirror convergence control configured to receive said measured shift in convergence from said top and bottom line correlators, and to adjust said control of said X-direction mirror drive by said FPGA, for said reflected line of light in said first direction to converge with said reflected line of light in said second direction;
   a top photodiode and a bottom photodiode each configured to receive infrared light of said raster pattern being reflected from the patient as a vasculature image, and to output a respective analog signal for said vasculature image;
   a top front end circuit and a bottom front end circuit, each configured to respectively receive said output signals of said top photodiode and said bottom photodiode; said top and bottom front end circuits configured to control analog filtering, gain, and threshold of said respective analog signals;
   a top analog-to-digital converter (ADC) and a bottom ADC configured to respectively receive said analog signals from said top and bottom front end circuits, and to convert said analog signals into digital signals, and to communicate said top and bottom digital signals to said FPGA;
   wherein said FPGA is configured to receive and process said top and bottom digital signals and to output a processed vasculature image; and
   wherein said red laser drive is configured to receive said processed vasculature image from said FPGA and to drive said red laser to project said processed vasculature image onto the patient.

2. The improved laser-based illumination system according to claim 1, wherein said top photodiode and said bottom photodiode are each configured to receive a full frame vasculature image of said reflected infrared light; and said system further comprising:
   a top histogram generator and a bottom histogram generator, each of said top and bottom histogram generators configured to generate a respective histogram of characteristics of said full-frame vasculature images; and an exposure control, said exposure control configured to receive said respective histograms and use said respective histograms to signal said infrared laser drive to adjust power to said infrared laser on a sequential frame by frame basis until said histograms indicate a proper image.

3. The improved laser-based illumination system according to claim 2, wherein said exposure control is further configured to signal said top and bottom front end circuits to therein adjust said control of gain and thresholds.

4. The improved laser-based illumination system according to claim 3, wherein said histogram characteristics comprise contrast and intensity levels.

5. The improved laser-based illumination system according to claim 1, further comprising:
   a top vein processing block configured to receive said top digital signal from said top ADC, and to perform imaging processing to detect vasculature patterns, and to provide an enhanced vasculature image;
   a bottom vein processing block configured to receive said bottom digital signal from said bottom ADC, and to perform imaging processing to detect vasculature patterns, and to provide an enhanced vasculature image; and
   a fused vein projection configured to receive said enhanced vasculature image from said top and bottom vein processing blocks, and to form a single enhanced digital vasculature image signal, said selective digital signal of said vasculature image output by FPGA comprising said single enhanced digital vasculature image signal.

6. The improved laser-based illumination system according to claim 5, wherein said single enhanced digital vasculature image signal formed by said fused vein projection is a formed signal from the group of formed signals consisting of:
   a merged signal formed by merging said top image signal and said bottom image signal; and
   a selected best image signal by selecting from either said top image signal or said bottom image signal.

7. The improved laser-based illumination system according to claim 6, further comprising a CPLD configured to control an LCD to display an operating status of said system thereon.

8. The improved laser-based illumination system according to claim 7, wherein said CPLD is further configured to control an audio output to provide audible tones.

9. The improved laser-based illumination system according to claim 8, wherein said CPLD is configured to control one or more switches on said system for turning on and off said system, for selecting one or more user modes, and for entering data therein.

10. The improved laser-based illumination system according to claim 9, further comprising a microprocessor configured to redundantly receive and monitor said IR laser feedback signal, said red laser feedback signal, said X-direction mirror feedback signal and said Y-direction mirror feedback signal, in conjunction with said FPGA.

11. An improved laser-based vasculature illumination system comprising:
   a field programmable gate array (FPGA);
   an X-direction mirror configured to oscillate about a first axis in a first direction and in a second direction, and an X-direction mirror drive means;
   a Y-direction mirror configured to oscillate about a second axis in a third direction and in a fourth direction, and a Y-direction mirror drive means;
   an X-direction mirror feedback means and a Y-direction mirror feedback means, each configured to detect a current respective mirror position and to signal said current position to said FPGA;
   an infrared laser and an infrared laser drive means, said FPGA configured to control said infrared laser drive means to control said infrared laser;
   an infrared laser feedback configured to detect the output of said infrared laser, and to signal said detected output to said FPGA;
   a red laser and a red laser drive means, said red laser configured to project a beam of light coaxially with a beam of light from said infrared laser, said FPGA configured to control said red laser drive means to control said red laser;
   a red laser feedback configured to detect the output of said red laser, and to signal said detected output to said FPGA;
   wherein said FPGA is further configured to control said X-direction mirror drive means for said X-direction mirror to reflect said coaxial beam of light in a line, in both said first direction and said second direction, and said FPGA further configured to control said Y-direction mirror drive means for said Y-direction mirror to oscillate about said second axis, to reflect said line of light to generate a raster;
   a top line correlator and a bottom line correlator, each said top and bottom line correlators configured to measure a respective shift in convergence between said reflected line of light in said first direction and said second direction, for each said oscillation of said X-direction mirror;
   a mirror convergence control, said mirror convergence control configured to receive said measured shift in convergence from said top and bottom line correlators, and to adjust said control of said X-direction mirror drive means by said FPGA, for said reflected line of light in said first direction to converge with said reflected line of light in said second direction;
   a first photodiode and a second photodiode each configured to receive infrared light of said raster pattern being reflected from the patient as a vasculature image, and to output a corresponding analog signal of said vasculature image;
   a first front end circuit and a second front end circuit, each configured to correspondingly receive said output signal of said first photodiode and said second photodiode; said first and second front end circuits configured to control analog filtering, gain, and threshold of said corresponding analog signals;
   a first analog-to-digital converter (ADC) and a second ADC configured to respectively receive said analog signals from said first and second front end circuits, and to convert said analog signals into digital signals, and to communicate said first and second digital signals to said FPGA;
   wherein said FPGA is configured to receive and process said top and bottom digital signals and to output a processed vasculature image; and
   wherein said red laser drive means is configured to receive said processed vasculature image from said FPGA and to drive said red laser to project said processed vasculature image onto the patient.

12. A laser-based vasculature illumination system comprising:
   a first laser configured to emit a beam of light at an infrared wavelength;

a first laser driver configured to control an output of said first laser to detect veins;

a first feedback means configured to detect said output of said first laser, and to provide said detected output as feedback;

a second laser configured to emit a beam of light at a red wavelength, to be co-axially aligned with said beam of infrared light;

a second laser driver configured to control an output of said second laser, and to provide said detected output as feedback;

a second feedback means configured to detect said output of said second laser;

a field programmable gate array (FPGA) configured to receive said output feedback from said first and second feedback means, said FPGA further configured to control said first laser driver and said second laser driver to respectively control said first and second lasers;

an x-direction mirror configured to reflect said coaxially aligned beam of light, and to pivot in a first direction and in a second direction about a first axis;

an x-direction mirror driver configured to control said x-direction mirror to oscillate about said first axis, to cyclically reflect said coaxially aligned beam of light in a line, in both said first direction and said second direction;

a first feedback means configured to detect a position of said x-direction mirror, and to communicate said position to said FPGA;

a line correlator configured to measure a shift in convergence between said reflected line of light in said first direction and said second direction, for each said oscillation of said X-direction mirror about said first axis;

a mirror convergence control, said mirror convergence control configured to receive said measured shift in convergence from said line correlator, and to adjust said control of said first mirror driver by said FPGA, for said reflected line of light in said first direction to converge with said reflected line of light in said second direction;

a y-direction mirror configured to reflect said line of light received from said x-direction mirror, and to pivot in a third direction and in a fourth direction about a second axis;

a second mirror driver configured to control said y-direction mirror to oscillate about said second axis, to reflect said line of light to form a raster pattern of said infrared light and red light;

a second feedback means configured to detect a position of said y-direction mirror, and to communicate said position to said FPGA;

a photodiode configured to receive a vasculature image formed from the infrared light of said raster pattern, said photodiode further configured to convert said vasculature image into an analog signal;

an analog-to-digital converter configured to receive said analog signal, and to convert said analog signal into a digital signal, and to communicate said digital signal to said FPGA;

wherein said FPGA is configured to receive and process said digital signal and to output a processed vasculature image; and wherein said second laser driver is further configured to receive said processed vasculature image and to drive said red laser to project said processed vasculature image using said x-direction mirror and said y-direction mirror.

* * * * *